United States Patent [19]
Greenleaf et al.

[11] Patent Number: 5,921,928
[45] Date of Patent: Jul. 13, 1999

[54] ACOUSTIC FORCE GENERATION BY AMPLITUDE MODULATING A SONIC BEAM

[75] Inventors: James F. Greenleaf; Mostafa Fatemi-Booshehri, both of Rochester, Minn.

[73] Assignee: Mayo Foundation for Medical Education and Research, Rochester, Minn.

[21] Appl. No.: 08/951,991

[22] Filed: Oct. 16, 1997

Related U.S. Application Data

[60] Provisional application No. 60/032,123, Dec. 5, 1996.
[51] Int. Cl.$^6$ ............................................. A61B 8/00
[52] U.S. Cl. ................................. 600/437; 600/443
[58] Field of Search .................... 600/437, 443; 367/7, 11, 103, 105; 73/625

[56] References Cited

U.S. PATENT DOCUMENTS

| | | | |
|---|---|---|---|
| 4,385,634 | 5/1983 | Bowen | 73/643 |
| 4,566,460 | 1/1986 | Sato et al. | 600/438 |
| 4,610,255 | 9/1986 | Shimira et al. | 600/438 |
| 5,099,848 | 3/1992 | Parker et al. | 73/575 |
| 5,606,971 | 3/1997 | Sarvazyan | 600/438 |
| 5,678,565 | 10/1997 | Sarvazyan | 600/437 |

OTHER PUBLICATIONS

J. Acoust; Acoustic Radiation Pressure in three–dimensional; Aug. 1, 1996; pp. 741–747.
Y. Wei and B. Gu; Acoustical Imaging, vol. 20; 1993; pp. 9–18.
T. Sugimoto, S. Ueja and K. Itoh; Ultrasonics Symposium; 1990; pp. 1377–1380.
J. Acoust; Calculation of acoustic radiation force gen.; May 1, 1995; pp. 2747–2750.
G.R. Torr; The Acoustic radiation force; May 5, 1984; pp. 402–408.
M.C. Ziskin and P.A. Lewin; Ultrasonic Exposimetry; 1993; pp. 127–142.

*Primary Examiner*—Francis J. Jaworski
*Attorney, Agent, or Firm*—Quarles & Brady, LLP

[57] ABSTRACT

A force is produced within an object by an ultrasonic beam. The frequency of this force is equal to the frequency of a signal used to modulated the amplitude of the beam. The sonic waves produced by the object in response to the force can be used to detect the presence of objects or to image objects based on their mechanical properties. It can also be used to regenerate a desired audio signal in the object.

12 Claims, 2 Drawing Sheets ns of ultrasound can be used to produce images of objects within a patient. The ultrasound transmitter may be placed on one side of the object and the sound transmitted through the object to the ultrasound receiver placed on the other side ("transmission" mode). With transmission mode methods, an image may be produced in which the brightness of each image pixel is a function of the amplitude of the ultrasound that reaches the receiver ("attenuation mode"), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude of the ultrasound reflected from the object back to the receiver ("reflection", "backscatter" or "echo" mode). In another mode of operation ("Doppler" mode) the movement of the object is detected and imaged by measuring the phase of the ultrasound reflected from the object back to the receiver.

ACOUSTIC FORCE GENERATION BY AMPLITUDE MODULATING A SONIC BEAM

RELATED APPLICATION

This application is based upon United States provisional application Ser. No. 60/032,123 filed on Dec. 5, 1996.

STATEMENT OF GOVERNMENT INTEREST

This invention was made with U.S. Government support awarded by the National Institute of Health (NIH) Grant No. CA 43920. The U.S. Government has certain rights in this invention.

BACKGROUND OF THE INVENTION

The field of the invention is the detection and imaging of objects using acoustic beams.

In the field of medical imaging there are a number of modes in which ultrasound can be used to produce images of objects within a patient. The ultrasound transmitter may be placed on one side of the object and the sound transmitted through the object to the ultrasound receiver placed on the other side ("transmission" mode). With transmission mode methods, an image may be produced in which the brightness of each image pixel is a function of the amplitude of the ultrasound that reaches the receiver ("attenuation mode"), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude of the ultrasound reflected from the object back to the receiver ("reflection", "backscatter" or "echo" mode). In another mode of operation ("Doppler" mode) the movement of the object is detected and imaged by measuring the phase of the ultrasound reflected from the object back to the receiver.

In all of these medical imaging applications ultrasonic waves are transmitted and ultrasonic waves are received. The higher sonic frequencies enable precise beams to be formed in both the transmit and receive modes. Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage waveform is applied, the piezoelectric elements change in size at a frequency corresponding to that of the applied voltage. When a voltage waveform is applied, the piezoelectric elements emits an ultrasonic wave into the media to which it is coupled at the frequencies contained in the excitation waveform. Conversely, when an ultrasonic wave strikes the piezoelectric element, the element produces a corresponding voltage across its electrodes. A number of such ultrasonic transducer constructions are disclosed in U.S. Pat. Nos. 4,217,684; 4,425,525; 4,441,503; 4,470,305 and 4,569,231.

When used for ultrasonic imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave that travels along a preferred beam direction and is focused at a selected point along the beam. By controlling the time delay and amplitude of the applied voltages, the beam with its focal point can be moved in a plane to scan the subject. A number of such ultrasonic imaging systems are described in U.S. Pat. Nos. 4,155,258; 4,155,260; 4,154,113; 4,155,259; 4,180,790; 4,470,303; 4,662,223; 4,669,314; 4,809,184; 5,081,995 and 5,492,121.

The acoustic radiation force exerted by an acoustic wave on an object in its path is a universal phenomenon common to all forms of radiated energy. When a beam of light is absorbed or reflected by a surface, a small force is exerted on that surface. The same is true for electromagnetic waves, transverse waves on an elastic string, and surface waves on a liquid. This force is produced by a "radiated pressure" and a complete disclosure of this phenomenon is set forth by G. R. Torr, "The Acoustic Radiation Force", *Am. J. Phys.* 52(5), May 1984.

The measurement of radiation force exerted by sound waves has become important in recent years to determine the power outputs of medical imaging ultrasonic transducers, Beissner, K., "Measurement Techniques In Ultrasonic Exposimetry," eds. M. C. Ziskin and P. A. Lewin, CRC Press, Boca Raton, 1993. The transducer is submerged in a tank of water and the ultrasonic beam is directed towards an absorbing or reflecting target in the tank. An absorbing target may be realized by a slab of natural rubber, or a reflecting target by an air-backed thin metal plate. If the ultrasonic beam is directed horizontally, the force can be determined by suspending the target as a pendulum and measuring its deflection. The measurements are made in water because the characteristic acoustic impedances of water and human soft tissue are similar, thus the measured ultrasonic beam power is virtually equal to the power radiated by the transducer into the human body provided that the effect of tissue loss has been accounted for.

It is generally accepted that the radiation force F exerted on a totally absorbing target by an ultrasonic beam of power P is given by the equation $$F = P/c,$$

where c is the speed of sound in the medium surrounding the target. For normal incidence on a plane reflecting surface the radiation force has twice this value. The speed of sound in water is 1500 m/s, thus the radiation force on an absorbing target in water is about $6.67 \times 10^{-4}$ newtons/watt.

This sonic radiation force has found application in medicine in the field of extracorporeal shock wave lithotripsy. By applying a set of powerful acoustic shock waves at the surface of the patient such that their energies focus on a target inside the patient, objects such as renal or gall-stones can be fragmented. Such lithotripsy systems are described, for example, in Goldstein, A., "Sources of Ultrasonic Exposure," *Ultrasonic Exposimetry*, eds. M. C. Ziskin and P. A. Lewin, CRC Press, Boca Raton, 1993.

Another application which employs an ultrasonic radiation force produced by a transducer is disclosed by Sugimoto et al, "Tissue Hardness Measurement Using The Radiation Force Of Focused Ultrasound", *IEEE Ultrasonics Symposium*, pp. 1377–80, 1990. In this experiment, a pulse of focused ultrasonic radiation is applied to deform the object which is positioned at the focal point of the transducer. The deformation is measured using a separate pulse-echo ultrasonic system and the hardness of the deformed object is measured. Measurements are made based on the rate of object deformation as the acoustic force is continuously applied, or by the rate of relaxation of the deformation after the force is removed.

A similar system is disclosed by T. Sato, et al. "Imaging of Acoustical Nonlinear Parameters and Its Medical and Industrial Applications: A Viewpoint as Generalized Percussion", *Acoustical Imaging*, Vol. 20, pg 9–18, published in 1993 by Plenum Press. In this system a lower frequency wave (350 kHz) is produced to act as a percussion force, and an ultrasonic wave (5 MHz) is used in a pulse echo mode to produce an image of the subject. The percussion force is said to perturb second order nonlinear interactions in tissues, which reveal more structural information than the conventional ultrasonic pulse/echo system alone.

SUMMARY OF THE INVENTION

The present invention is a method and system for producing an acoustic radiation force at a target location by directing a high frequency sound beam at the location. The high frequency sound beam is amplitude modulated and a radiation force is produced at the location which varies in accordance with the amplitude modulation.

A general object of the invention is to detect or characterize an object based on its mechanical properties. An object at the location of the beam will respond to the applied acoustic radiation force by producing an acoustic wave that can be detected with a microphone or other detection apparatus. The detected acoustic wave may be used to detect the presence of the object or it may be used to detect and evaluate the mechanical properties of the object.

Another object of the invention is to produce an image of the target object. The high frequency sound beam may be moved to scan the object and signals indicative of the acoustic wave produced at each scanned location may be acquired. The acquired signals are used to produce an image of the object.

Another object of the invention is to project a force into an object to measure the object's mechanical characteristics. The radiation force produced by the high frequency sound beam produces motion at the location which can be detected and analyzed to measure the mechanical characteristics at that location. Detection can be performed in a number of ways, including Doppler ultrasound and nuclear magnetic resonance imaging.

Yet another object of the invention is to regenerate baseband audio at a remote location. By modulating the high frequency sound beam with a baseband audio signal, the radiation force at the location will vary as a function of the baseband audio signal and a corresponding acoustic wave is produced. By using the highly directional high frequency sound beam, therefore, a non-directional audio wave can be precisely produced at the location.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 1:
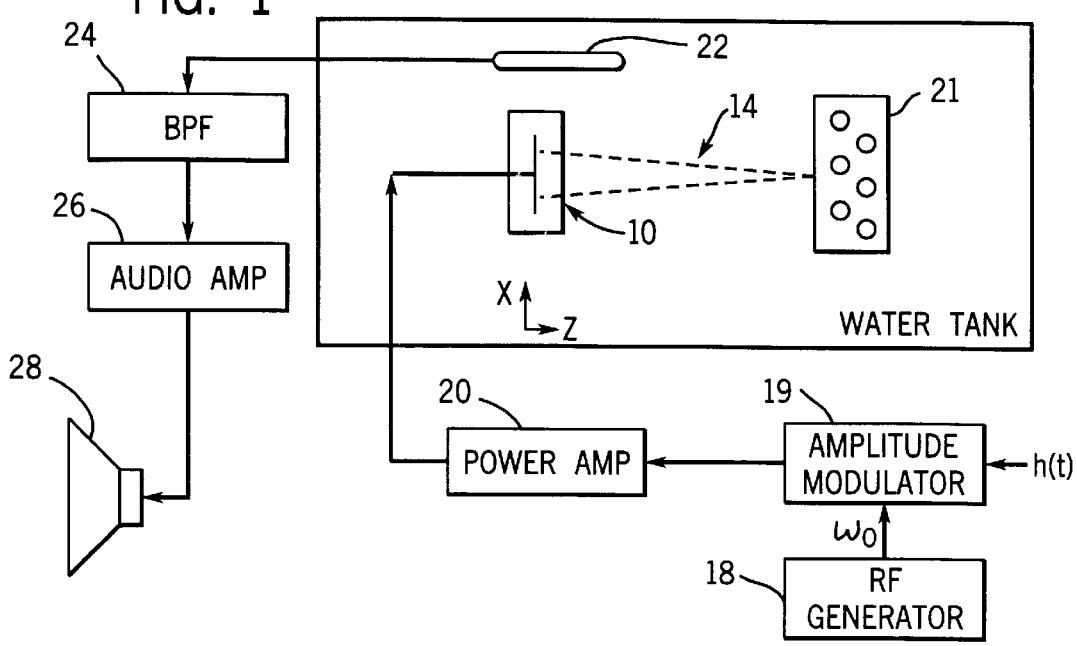
FIG. 1 is a block diagram of a first embodiment of the invention used to detect the presence of an object according to the present invention.

Consider an ultrasonic source directing its beam on a large target in water. The radiation force, F, for the plane wave case is commonly written as $$F = KP/c, \quad (1)$$

where P, c, and K are the time averaged acoustic power, sound speed in water, and a constant, respectively. The value of K for a perfectly absorbing target is 1, and for a perfectly reflecting target it is 2. For a focused beam impinging on a partially reflecting target of arbitrary size, the linear relation of (1) still holds, however, the value of K is different and can be determined as a function of target power reflection coefficient and its size as described by J. Wu, "Calculation of Acoustic Radiation Force Generated by Focused Beams Using the Ray Acoustic Approach," *J. Acoust. Soc. Am.* 97(5), pt. 1, May 1995.

In the present invention the high frequency field is generated by a single, ultrasonic source (single element or array of elements) driven by an amplitude modulated signal. The carrier frequency is $\omega_0$ and the modulating signal, h(t), is defined as:

$$h(t) = \sqrt{u(t)}, \quad (2)$$

where $$u(t) = 1 + f(t). \quad (3)$$

The signal f(t) is a low frequency signal. We assume |f(t)|<1, also we assume that the bandwidth of f(t) is much less than the carrier frequency $\omega_0$.

We assume the beam is propagating along the z-axis. The field on the z=0 plane can be written as $$s(t) = g(x,y)h(t)\cos(\omega_0 t), \quad (4)$$

where g(x,y) is the beam profile on the z=0 plane. It can be shown that the acoustic power density has slow variations about its long time average. Denoting this component by $P_1(t,x,y)$, we can write $$P_1(t, x, y) = \frac{1}{2}g^2(x, y)h^2(t). \quad (5)$$

Assuming a target is present at z=0 plane, then referring to Equation (1), the radiation force exerted on this target by $P_1(t,x,y)$ may be found by the following integration:

$$F_1(t) = \frac{K}{c}\int\int P_1(t, x, y)dx\,dy. \quad (6)$$

The result of this integration is a function proportional to $h^2(t) = 1 + f(t)$. The time-varying component of this force vibrates the target proportional to the signal f(t). The target displacement due to this force, r(t), may be written as $$r(t) = \frac{1}{2}K'f(t) \quad (7)$$

where K' is a constant whose value depends on size, power reflection coefficient, and other mechanical parameters of the target, such as mass and damping factors, that determine its response to a given force.

Within the target area the force indicated by Equation (6) will be applied to the object. The manner in which the object responds to this force will, of course, depend on its mechanical characteristics. As the embodiments of the invention described below will indicate, there are many uses for this invention which stem from its ability to accurately project a low frequency acoustic force to a defined area.

The response of an object to the radiation force may be explained by considering a simplified, one-dimensional equation of motion for the mass-spring model. In this model, we assume a mass m is held by a spring having a "stiffness constant" of $\mu$. We also assume that motion of this mass is damped by friction or by other mechanisms represented by the "resistance constant" $R_m$. Now consider a sinusoidal force $F_1(t)=A \cos \omega_m t$ being applied to this mass. As described by P. M. Morse and K. V. Ingard, "Theoretical Acoustics," McGraw Hill, 1968, the steady-state motion of the mass due to this force can be written as:

$$x(t)=A \cos(\omega_m t+\phi)/\omega_m|Z_m|$$

where $$Z_m=R_m-j(\omega_m-\mu/\omega_m)$$

is the mechanical impedance, and $$\tan \phi=(\omega_m-\mu/\omega_m)R_m$$

Thus the amplitude and phase of the displacement of the mass are determined by the mechanical properties m, $R_m$ and $\mu$. At its resonant frequency, where $\omega_m=\sqrt{\mu/m}$, the amplitude of the motion reaches its maximum value.

DESCRIPTION OF THE PREFERRED EMBODIMENT

Referring particularly to FIG. 1, a first embodiment of the invention is used to detect the presence of an object based upon the acoustic wave produced by the object in response to the applied force $F_1(t)$. This detector system includes an ultrasonic transducer 10 which produces a focused beam 14 of beamwidth w=2 mm at its focal point. The transducer 10 is driven by an RF generator 18 that produces an ultrasonic frequency $\omega_0=2\pi\times3,500,000$ rad./sec. This carrier signal $\omega_0$ is applied to an amplitude modulator 19 which also receives the modulating signal h(t). Here we assume f(t)=cos $\omega_m t$, where $\omega_m<<\omega_0$. The modulated carrier is amplified in power amplifier 20 and applied to the transducer 10.

The acoustic field produced by the object 21 in response to the force produced by the focused beam 14 is received by a hydrophone 22. The received signal is applied through a band-pass filter 24 to an audio amplifier 26. The band-pass filter 24 has a narrow pass band centered on $\omega_m$ to reject noise and any reflected ultrasonic signals. The amplified audio signal may be applied to a loudspeaker 28 or an earphone to provide the operator with an indication of the amplitude of the acoustic wave produced by the object 21. The transducer 10 can be moved physically to scan the object 21, or in the alternative the beam 14 can be steered electronically to scan the object 21. An alternative choice for h(t) can be, for example, h(t)=cos $\omega_m t$. In this case, the acoustic field produced by the object is proportional to the cos $2\omega_m t$. In this case the band pass filter 24 must be centered around $2\omega_m$.

A second embodiment of the invention is a novel imaging system. Rather than relying on the reflection or attenuation of an ultrasonic wave by the object as is done in ultrasound imagers, the imager of the present invention relies on other mechanical properties of the object. More specifically, the ability of the object to convert the force $F_1(t)$ to an acoustic wave that can be detected by the receiver.

Figure 2:
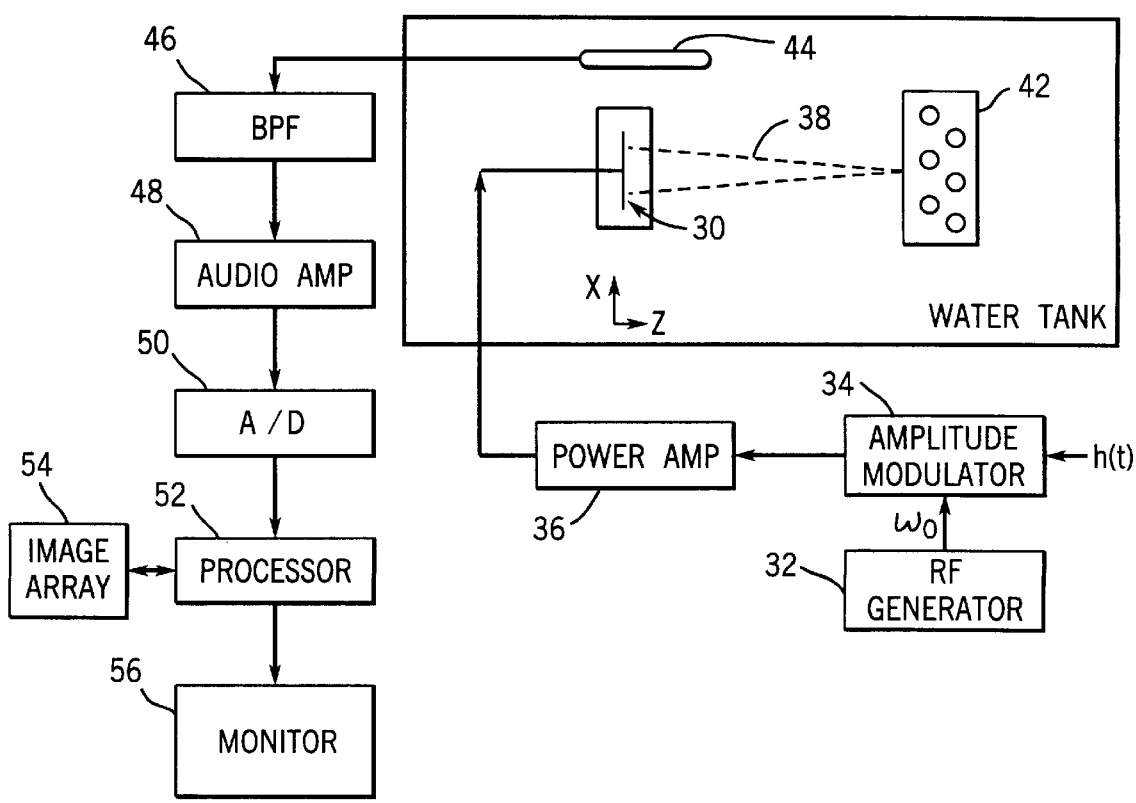
FIG. 2 is a block diagram of a second embodiment of the invention used to image an object according to the present invention.

Referring particularly to FIG. 2, the imaging system includes a focused transducer 30 which produces a beam 38 which has a focal region from 6 cm to 13 cm, and a beamwidth of w=2 mm (defined as the full-width at half-maximum). The transducer 30 is driven by an RF generator 32 which produces a carrier signal $\omega_0=2\pi\times3,500,000$ rad./sec. The carrier signal $\omega_0$ is amplitude modulated at 34 by a modulating signal h(t), and the modulated carrier is amplified by power amplifier 36.

The sonic wave produced by the target object 42 in response to the force $F_1(t)$ is received by a hydrophone 44 and digitized. The receiver signal is filtered by a band-pass filter 46 centered on the frequency of the signal h(t), amplified at audio amplifier 48 and digitized by a 12-bit analog-to-digital converter 50 at 100,000 samples/sec. The processor 52 calculates the mean amplitude (or the standard deviation) and/or phase of 600 samples of the digitized signal, then stores this value in the image array 54 at a location corresponding to the position of the focal spot of beam 38. Processor 52 also controls other parts of the system to carry out the scan process. It steers the beam 38 to raster scan the object 42 in the x-y (or x-z) plane. Beam steering is accomplished either mechanically using two stepper motors (not shown), or by well known phased array techniques. Processor 52 also provides the trigger signals needed to synchronize the scanning and digitization function. The resulting image produced after a complete raster scan may be enhanced using known image enhancement methods and/or displayed on a monitor 56. A two-dimensional image is thus produced in which the gray scale intensity of each pixel indicates the acoustic level and/or phase produced by the target 42 in response to the applied force $F_1(t)$.

A variation of this two-dimensional imaging system can be used to acquire a three-dimensional image in which two dimensions are spatial (x,z) and the third dimension is modulation frequency amplitude. In this alternative, the signal f(t) is swept through a range of modulation frequencies. The acquired signal samples at each x,z beam location are stored at successive frequency bins in the image array 54. The resulting frequency dimension provides the information needed for analyzing the spectrum of the object's acoustic response to mechanical stimulations at different frequencies.

As an example application, one can make use of this method to identify calcification in tissue and estimate its thickness and size. Referring to the mass-spring model described above, the amplitude of the motion peaks at the resonant frequency, and this is proportional to $1/\sqrt{m}$. Calcification with different thicknesses have different masses, thus resonating at different frequencies. Hence, when examining different regions of calcification by the variable modulation frequency method, one can expect to see peaks at different frequency bins depending on the thickness and size of the calcification.

Other imaging modalities can also be used to measure the motion resulting from the radiation force produced by the present invention. For example, a magnetic resonance imaging ("MRI") system, such as that described in co-pending U.S. patent application Ser. No. 325,834 filed Oct. 19, 1994 and entitled "MR Imaging of Synchronous Spin Motions And Strain Waves" can be used to image the mechanical characteristics of the scanned object. In this system a motion sensitizing magnetic field gradient on the MRI system is synchronized with the applied radiation force (i.e. the signal f(t)) and the resulting motion is precisely indicated by the phase of the acquired NMR signals. As described in this co-pending application which is incorporated herein by reference, nearly all mechanical properties of the imaged object can be measured and used to modulate the intensity of a reconstructed image. This method can be used to provide a map of tissue stiffness which is an excellent tool to detect deep tumors. Again, an alternative choice for h(t) is h(t)=cos $\omega_m t$ in which case the acoustic field is proportional to cos $2\omega_m t$. In this case the band pass filter is centered around $2\omega_m$ rather than $\omega_m$.

A third embodiment of the invention serves an entirely different function than those described above. Rather than obtaining an indication of the presence or nature of a target object, in the third embodiment of the invention information is transferred to the target object in the form of acoustical energy. By using an ultrasonic beam which can be finely focused and directed, this transfer of information can be precisely targeted.

Figure 3:
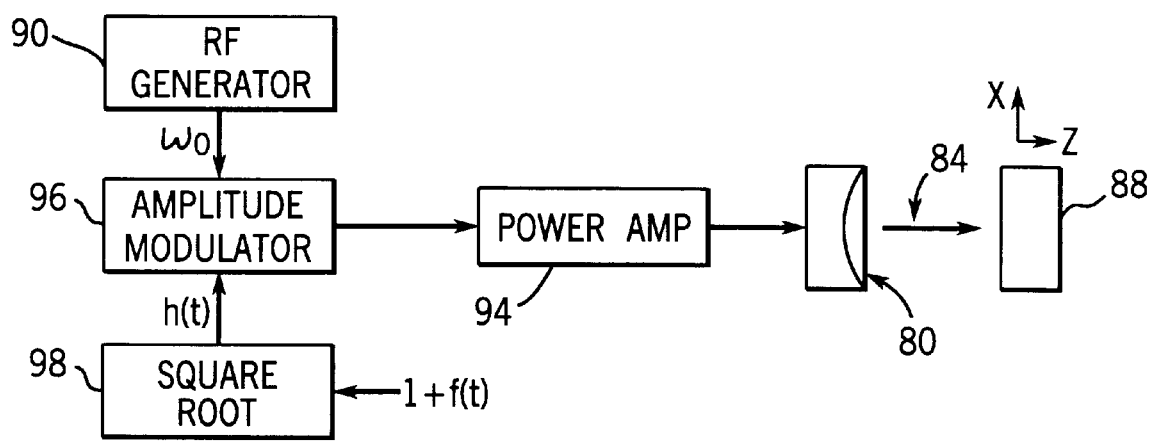
FIG. 3 is a block diagram of a third embodiment of the invention used to convey a signal acoustically to a distant target object according to the present invention.

Referring particularly to FIG. 3, the audio regeneration system includes an ultrasound transducer 80 that produces a beam 84 which focuses on a target object 88. The beam width at its focal point is w=2 mm. The transducer 80 is driven by an RF generator 90 which produces a high frequency carrier signal $\omega_0$ at a frequency of 3.5 MHz. The carrier signal $\omega_0$ is applied to an amplitude modulator 96 which also receives a modulating signal h(t). The output of the modulator 96 (h(t)cos(($\omega_0$t)) is applied through a power amplifier 94 to the transducer 80.

The modulating signal h(t) is produced by a square root circuit 98. It receives as its input the baseband signal f(t) plus "1". The baseband signal f(t) is less than "1".

The ultrasonic beam 84 causes the target object 88 to vibrate in response to the baseband signal f(t). The beam 84 is made very directive because the wavelength of the ultrasound beam at carrier frequency $\omega_0$ is very small compared to that of the baseband signal f(t). The target 88 acts as the converter of the high frequency ultrasound energy to the baseband frequency energy and the frequency response can be made very flat because the bandwidth of the baseband signal f(t) is very small relative to the ultrasound carrier frequency $\omega_0$.

One medical application of this embodiment of the invention is a hearing aid. The transducer is positioned along side the user's temple and the ultrasonic beam is directed to structures in the inner ear. The baseband signal f(t) is the ambient sound picked up by a microphone and amplified. This ambient sound is reproduced in the inner ear by vibrating structures in the inner ear. The eardrum and the middle ear are completely by-passed by this sound regeneration system, and patients with hearing loss due to problems in these structures can be helped.

While in many medical applications the transducer is positioned outside the patient and directs ultrasound into an object in the patient, it is also possible to place the transducer inside the patient. For example, the transducer may be mounted on the end of a catheter as described, for example, in U.S. Pat. No. 5,345,940 and inserted into the patient through the vascular system. This enables the transducer to be positioned closer to the target object.

The invention can be used to remotely measure the elastic constants of a material. For example, a swept frequency force can be applied to a metallic rod to measure its resonant frequency. The resonant frequency can be used to accurately measure the Young's modulus of the rod material.

The invention can also be used for accurate and remote measurement of the sheer viscosity, or the density, of a liquid. This can be done by aiming the ultrasound beam on a well characterized tuning fork immersed in the liquid. The sheer viscosity or the density can be measured accurately and remotely by measuring the shift in the resonant frequency of the tuning fork with respect to its natural resonant frequency in vacuum.

We claim:

1. A detector system for indicating the presence of an object, the combination comprising:

a sonic beam producer for producing a sonic beam at a high frequency $\omega_0$ which is directed at the object;

an amplitude modulator for supplying a signal to the sonic beam producer at the high frequency $\omega_0$ which is modulated in amplitude at a modulation frequency; and a detector for receiving a sonic wave produced at the modulation frequency by the object and the detector having means for indicating the presence of the object in response to the received sonic wave.

2. The detector system as recited in claim 1 in which the modulation frequency is within the audible hearing range of humans and the detector indicates its presence by producing an audible sound.

3. The detector system as recited in claim 1 in which the modulation frequency is swept through a range of frequencies such that the frequency of the sonic wave is also swept through a range of frequencies.

4. The detector system as recited in claim 1 in which the object is located within a human subject and the sonic beam producer and the detector are located outside the human subject.

5. A detector system for indicating the mechanical characteristics of an object, the combination comprising:

a sonic beam producer for producing a sonic beam at a high frequency $\omega_0$ which is directed at the object;

an amplitude modulator for supplying a signal to the sonic beam producer at the high frequency $\omega_0$ which is modulated in amplitude to produce a force in the object corresponding to the modulating signal; and means for detecting motion in the object caused by the force.

6. The detector system as recited in claim 5 in which the means for detecting is an ultrasonic Doppler system.

7. The detector system as recited in claim 5 in which the means for detecting is a nuclear magnetic resonance system.

8. The detector system as recited in claim 5 in which the frequency of the modulating signal is varied over a range of frequencies such that the frequency of the force is also varied over a range of frequencies.

9. The detector system as recited in claim 5 in which the object is located within a human subject and the sonic beam producer and the means for detecting are located outside the human subject.

10. The detector system as recited in claim 1, further comprising:
   means for moving the sonic beam to scan its focal point over a region in the object to be imaged, wherein said detector receives said sonic wave produced at the modulating frequency by the object as said sonic wave is scanned and said detector produces an output signal indicative of the amplitude of the sonic wave; and
   a display for receiving the output signal and producing an image indicative of the amplitude of the sonic wave emanating from locations in said region.

11. The detector system as recited in claim 10 in which the object is located within a human subject and the detector system is located outside the human subject.

12. The detector system as recited in claim 10 in which the modulating frequency is changed over a range of values as the focal point scans the region to be imaged, and the detector receives the sonic waves produced at the corresponding frequencies.

* * * * *